(12) United States Patent
Di Massa

(10) Patent No.: US 6,213,766 B1
(45) Date of Patent: Apr. 10, 2001

(54) MODULAR MULTIFUNCTIONAL APPARATUS FOR DENTO-MAXILLO-FACIAL ORTHODONTICS AND ORTHOPEDICS

(76) Inventor: Elisabetta Di Massa, Via Corsica 40, 86039 Termoli (IT)

( * ) Notice: Subject to any disclaimer, the term of this patent is extended or adjusted under 35 U.S.C. 154(b) by 0 days.

(21) Appl. No.: 09/256,589

(22) Filed: Feb. 23, 1999

(30) Foreign Application Priority Data

Mar. 10, 1998 (IT) .............................................. FI98A0054

(51) Int. Cl.[7] .............................................. A61C 3/00
(52) U.S. Cl. .............................................................. 433/7
(58) Field of Search ....................................... 433/7

(56) References Cited

U.S. PATENT DOCUMENTS

| | | | |
|---|---|---|---|
| 1,582,570 | * 4/1926 | Brust | 433/7 |
| 3,162,948 | * 12/1964 | Gerber | 433/7 |
| 3,835,540 | 9/1974 | Biederman | 433/7 |
| 4,571,177 | 2/1986 | Dahan | 433/7 |
| 4,592,725 | * 6/1986 | Goshgarian | 433/7 |
| 4,597,738 | * 7/1986 | Sander et al. | 433/7 |
| 5,002,485 | * 3/1991 | Aagesen | 433/7 |
| 5,007,828 | * 4/1991 | Rosenberg | 433/7 |
| 5,895,217 | * 4/1999 | Kooiman | 433/7 |

\* cited by examiner

Primary Examiner—John J. Wilson
(74) Attorney, Agent, or Firm—McGlew and Tuttle, P.C.

(57) ABSTRACT

An apparatus is disclosed for dento-maxillo-facial orthodontics and orthopedics. The apparatus includes a base structure (1) able to be fixed to lateroposterior teeth (2) of the superior arch transversally to the sagittal plane (s—s) in correspondence of the palatal vault. The base structure (1) exhibits a plurality of arms (10) developed orthogonally to the plane (s—s) and at ends of which corresponding annular bands (11) are provided to allow a stable positioning thereof on said teeth (2). A device is provided for the removable or irremovable fastening of one or more orthodontic or orthopedic modules which are, in turn, provided with a portion able to be engaged with this fastening device of the base structure (1).

17 Claims, 3 Drawing Sheets

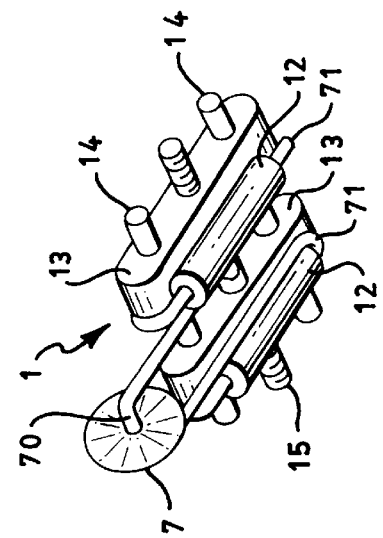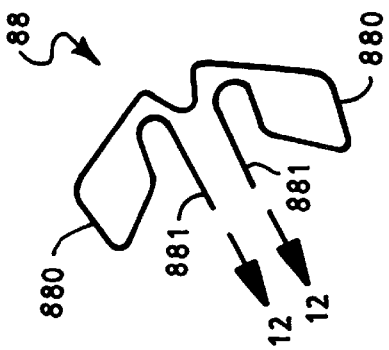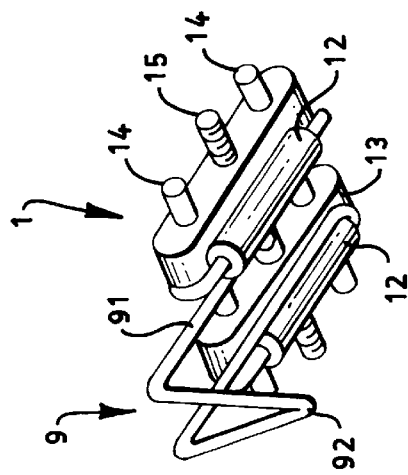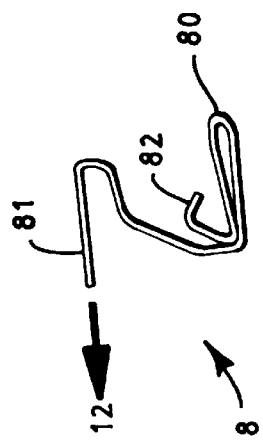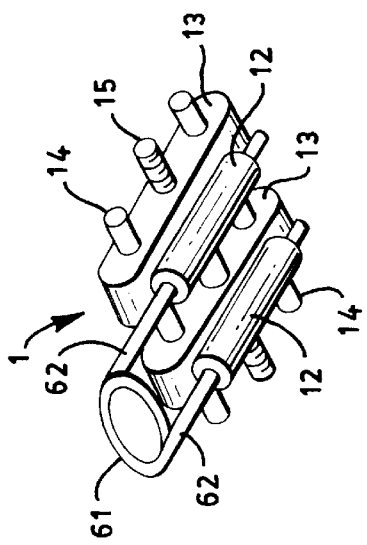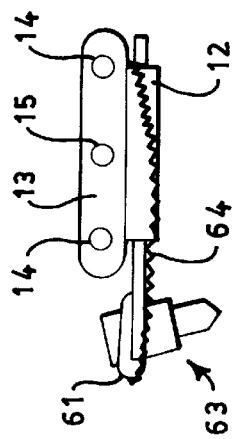

MODULAR MULTIFUNCTIONAL APPARATUS FOR DENTO-MAXILLO-FACIAL ORTHODONTICS AND ORTHOPEDICS

FIELD OF THE INVENTION

The present invention refers to a modular multifunctional apparatus for dento-maxillo-facial orthodontics and orhtopedics.

BACKGROUND OF THE INVENTION

It is kniwn to those skilled in the art that "fixed" or "mechanical" orthodontic therapies provide, essentially, for the application of a force, having predetermined intensity and direction, on each tooth of the arches under corrective treatment, so as to determine their slow and gradual displacement within respective alveoli until they reach a position that would be judged optimal as a whole by an orthodontist.

In case of intraoral devices with vestibular action, the corrective forces are applicable, for example, by means of a plurality of attachments able to be fixed to the vestibular and lingual versants of the teeth and interconnected by elastic members such as preformed arches and springs. Said elastic members are intended to generate the forces—of reactive nature, owing to the deformation they are subjected to upon use—to be applied to the teeth in correspondence of the attachements location.

The orthopedic therapies for the correction of dento-facial disfunctions make it possible, by modulating the forces applied on the teeth so as to transmit the same forces more deeply, to intervene on the osseous structure so as to change its arrangement to a more or less extent depending on the gravity and nature of the intervention, that is, of the malformation to be treated. In the case, for example, of orthopedic procedures for the rapid expansion of the palate, apparatus are used able to open the mid-palatine suture directly and the adjacent sutures indirectly, for the correction of superior maxilla's deficit. These apparatus comprise, essentially, an expansion screw, also said "disjunctor", having side arms connected to latero-posterior teeth of the superior arch by bands of metallic material, such as the LEONE screw model A 620 or the screws disclosed in U.S. Pat. Nos. 3,835,540 and 4,571,177.

The upper maxilla is fixed and solid to the rest of the skull. The mandibula is the only movable bone of the skull and, because of its structure, is unsuitable for orthopedics as conventionally applied to the maxilla. Accordingly, the orthopedics of the mandibula is carried out by exploiting the mobility of the latter through some conditionings of its position and, therefore, of its function. This has such biological effects on the mandibula and its relevant functions, as those caused by the disjunctor on the superior maxilla. This is why reference is made to "functional" orthopedics whenever use has been made in the oral cavity of removable and irremovable apparatus generally made of acrilic resins and able to condition the mandibular position, usually under protrusion. In fact, the structural advancement of the mandibula is usually requested in cases of second-class maloclusions in which, typically, one resorts to orthopedic therapy with movable apparatus.

Conventional corrective therapies, both of orthodontic and orthopedic kind, make use of apparatus, for example of the type above described, especially constructed for application thereof in different times, that is, with separate intervention procedures and such, anyway, that the therapeutic times add to one another when the need arises for both orthopedic and orthodontic intervention, which brings about an excessive and prolonged discomfort also of psycological character for the patient.

SUMMARY AND OBJECTS OF THE INVENTION

The main object of the present invention is to overcome the said drawbacks.

The advantages deriving from the present invention lie essentially in that it is possible to provide at the same time maxillary and madibular orthopedics on fixed apparatus, with considerable reduction of the therapeutic times; that it is possible to associate to known supports a plurality of different, intraoral or extraoral orthodontic devices, both of functional and mechanical or fixed type, each of which being constructed and dimensioned to carry out a corresponding corrective function, that is, able to apply sheer, global and/or sectorial orthodontic forces, onto one or both semiarches, with the possibility of synergically combining the orthodontic action with the orthopedic one; that the present apparatus can support modular elements able to exert a tridimensional control of all the mandibular, maxillary and occlusal components, said control making it possible to reach an optimal morpho-functional coordination and a correct relationship of the cranio-mandibulo-cervico-rachi-postural system; that the present appartus is able to support diagnostic instruments such as points for recording the mandibula's position and path; that the apparatus according to the invention is simple to make, cost-effective and reliable even after a prolonged service life.

BRIEF DESCRIPTION OF THE DRAWINGS

These and other advantages and characteristics of the invention will be best understood by anyone skilled in the art from a reading of the following description in conjunction with the attached drawings given as a practical exemplification of the invention, but not to be considered in a limitative sense, wherein:

FIGS. 3a and 3b are respectively a perspective view and a sagittal section view of the apparatus provided with a recording device associated to the module of FIG. 2d, in operating condition;

FIG. 4 shows an apparatus according to the invention provided with a module for supporting a "Tucat pearl";

FIGS. 5a and 5b show an interocclusal spacer, respectively of monolateral and bilateral type;

FIG. 6 shows an apparatus according to the invention provided with a mandibular conditioning module.

DESCRIPTION OF THE PREFERRED EMBODIMENTS

Figure 1B:
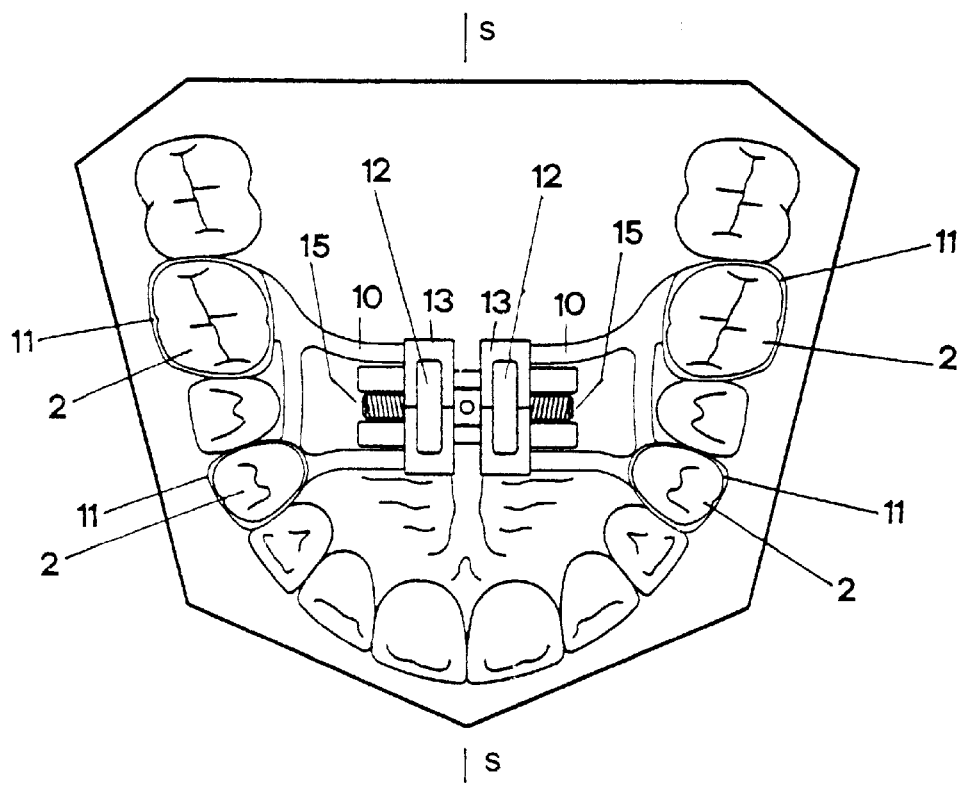
FIGS. 1a and 1b are rear view and a bottom view of an apparatus according to the invention in operating condition.
Figure 1A:
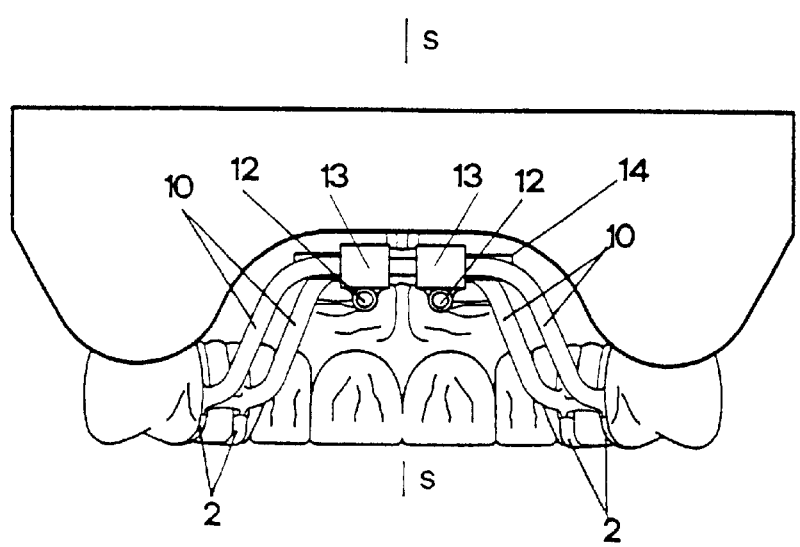

Reduced to its basic structure, and reference being made to the figures of the attached drawings, a modular multifunctional apparatus according to the invention comprises a base structure (1) able to be fixed to latero-posterior teeth (2) of the superior arch transversally to the sagittal plane (s—s)

in correspondence of, but not in contact with, the palatal vault. The base structure (1) exhibits a plurality of arms (10) developed orthogonally to said plane (s—s), the ends of which arms being provided with corresponding annular bands (11) to allow a stable positioning thereof on said teeth (2). The structure (1) is provided, in correspondence of its lingual versant, with two cylindrical bushes (12) parallel and equidistant to the plane (s—s). The two bushes allows the base structure (1) to be connected to a plurality of devices each having a predetermined therapeutic or diagnostic function, as described in more detail later on, at a well defined position of the palatal vault.

Figure 2A:
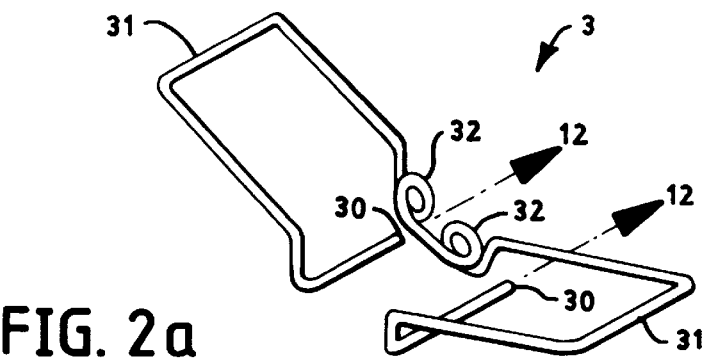
FIGS. 2a–2d show respectively in enlarged scale a bilateral mandibular condylar distractor module, a module for extra-oral postero-anterior traction, a lingual grid and a support module for mandibular path-recording device, said modules being connectable to the apparatus of FIGS. 1a and 1b.
Figure 2B:
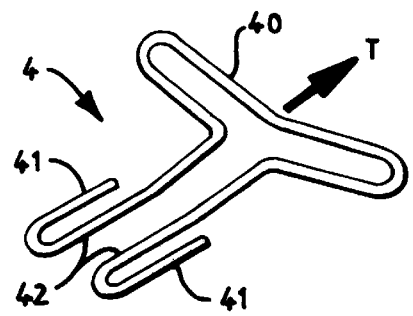
Figure 2C:
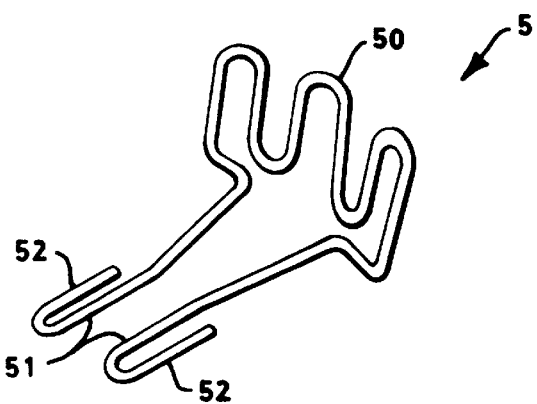
Figure 2D:
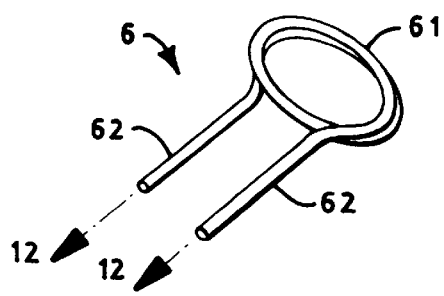

According to a particularly advantageous embodiment, the base structure (1) is made up of an expansion screw, for example, of LEONE type model A 620, with two movable blocks (13) guided by two straight rods (14) and associated to the screw drive (15) which engages axially the two blocks (13). The movement of the two blocks (13) guided on the rods (14) by the screw (15) brings about the corresponding movement of the osseous structures leading to the teeth (2), on which teeth the bands (11) provided at the end of arms (11) are fitted. With reference to FIGS. 2a–4 of the attached drawings, the modules associable to the structure (1) in correspondence of the bushes (12) may exhibit, for example:

a bilateral mandibular condylar distractor module (3) to be used for distracting the mandibular condyle from its articular seat and thus promoting its relative growth (FIG. 2a). Said distractor (3) consists of a substantially filiform element of suitable diameter, with two free ends (30) each of which is intended to engage the cavity of a corresponding bush (12) of the base structure (1). Moreover, the distractor (3) exhibits two wings (31) for supporting the lower arch on the occlusal versant, each of said wings extending on one side transversally to a corresponding free end (30) and, on the opposite side joining without solution of continuity the other wing (31) through two coils (32) orthogonally aligned to the sagittal plane (s—s) in order to exert an elastic thrust on the mandibula through the lower arch with a condylar traction effect;

a device (4) for extra-oral postero-anterior traction (see FIG. 2b). This device is a filiform element of suitable diameter with a front portion, ring-like closed symmetrically with respect to the sagittal plane and apt to make up an anchoring element to exert a pull (T) in the postero-anterior direction to promote an equal advancement of the superior maxilla. The front part (40) of said module (4) joins up, without solution of continuity, with two straight and parallel portions (41) of the filiform element which are to engage corresponding cavities of the two bushes (12) of the base support (1) and whose corresponding extensions (42), projecting from said bushes (12) upon use, are bent through 180° to allow them to be hooked up to the structure (1) when necessary;

a lingual grid (5) (see FIG. 5) consisting of a filiform element whose front part (50) is cage-shaped to prevent the positioning of the tongue in correspondence of the dental arches, and extends rearwardly without solution of continuity so as to exhibit two straight portions (51) for engagement thereof into the cavities of said bushes (12). The extensions (52) of said portions (51) of module (5) are to be bent through 180°, likewise in the example previously described, to have them hooked up the base structure (1) of the apparatus;

an apparatus for recording the mandibular path, with a filiform body (6) of suitable diameter exhibiting a dual front coil (61) whose two straight ends (62) are intended for fitting into respective cavities of the bushes (12) of the base structure (1) (FIGS. 2d–3b). The front part (61) of said module (6) delimits a seat for mounting the point (63) provided for recording the patient's mandibular movement on a disc (not represented in the attached drawings) having a layer of wax thereon and positioned in the patient's mouth on the opposite side of the structure (1). Said point (63) is able to be removably fixed to the assembly (1; 6) by means of an elastic (64) which embraces both the point (63) and the structure (1);

a device for lingual reeducation consisting in a roller (7) to be rotated about a horizontal axis (70) by the tongue. The axis (70) of said lingual reeducation module is made up of a filiform element which extends bilaterally and rearwardly. The lateral extensions (71) of said axis (70) are intended for positioning, inside the cavities of bushes (12), the main body (1) and for hooking up said body (1) upon the bending thereof through 180° performed by the doctor;

a monolateral interocclusal spacer consisting of a filiform element bent over through 180° in correspondence of the portion (80) making up the very spacer, with a free straight end (81) to be received in a corresponding bush (12) of structure (1) and with a hook (82), formed by the extension of said portion (80), to allow a further fastening thereof by means of an elastic;

a bilateral interocclusal spacer (88) (see FIG. 5b) consisting of a filiform element with two side portions (880) forming the required thicknesses and with two straight substantially parallel appendixes (881) to be received into the corresponding bushes (12);

a mandibular conditioner (9) (see FIG. 6). This is a filiform element of suitable diameter with two straight portions (90) to be received into respective bushes (12) of the structure (1) and joined by a "V" portion (91) having the vertex facing the lower arch upon use of the apparatus. The V-shaped element (92) is intended to strike the lingual surface of the lower alveolar process, either directly or with the interposition of other apparatuses able to create a protective thickness suach as the one of a lingual plate or lingual arch. The said conditioning module (9) is intended to condition the position of the mandibula, mostly according to a sagittal plane, and its relationship with the cranio-maxillary system.

It will appear evident from the above that to the base body (1) it is possible to associate a plurality of modules, each of which being constructed to carry out a specific therapeutic function. In this sense, the present apparatus is modular and multifunctional.

Also connectable to the structure (1) are cephalea-treatment elements, such as the interocclusal spacers known per se to those skilled in the art, which elements, likewise the previously mentioned modules, interfere with the mandibulo-maxillo-cranial relationship.

It is understood that more modules are associable to the body (1) at the same time. In this case, the means for anchoring the modules to the base body (1) may comprise more than two bushes (12).

Advantageously, according to the invention, said bushes may be oriented either parallel to the sagittal plane (s—s), and positioned symmetrically with respect thereto, or in such a way that their respective axes will form a given angle to said plane, and the same bushes will result positioned asymmetrically thereto.

This allows the corrective forces to be exerted upon the semiarches, or upon the dental sector and elements associated to the apparatus, at predetermined sites of the dento-faccial structure, and with such an orientation as to provide a simultaneous and synergic action.

It will also be evvident from the above description that if the base body (1) is an expansion screw, or a palatal separator, and one or more modules connected thereto are devices intended to perform different corresponding terapeutic actions, both of orthodontic and orthopedic nature, the duration of the treatment the patient is subjected to, will result significantly reduced. Also evident is the fact that if the base body (1) is not a palatal separator but acts instead merely as a support for more operating module, the duration of the therapeutic action will result likewise reduced, besides being improved by the simultaneous and synergic action of the modules.

Practically, all the construction details may vary in any equivalent way as far as the shape, dimensions, elements disposition, nature of the used materials are concerned, without nevertheless departing from the scope of the adopted solution idea and, thereby, remaining within the limits of the protection granted to the present patent for industrial invention.

What is claimed is:

1. An apparatus for dento-maxillo-facial orthodontics and orthopedics, the apparatus comprising:
    a base structure with connection portions for fixing the base structure to latero-posterior teeth of the superior arch transversely to the sagittal plane in correspondence of the palatal vault, said base structure having a plurality of arms extending orthogonally to the sagittal plane and with said connection portions including annular bands provided to allow a stable positioning of an arm for applying force on respective said latero-posterior teeth of the superior arch transversely to the sagittal plane in correspondence of the palatal vault for orthopedic therapy;
    a connection device connected to said base structure; and
    one or more orthodontic or orthopedic module, said one or more module having a portion able to be engaged with said connection device for fastening said one or more module relative to said base structure, wherein said base structure includes an expansion screw with two movable blocks guided by two straight rods and associated with a screw drive which axially engages the two blocks.

2. An apparatus according to claim 1, wherein said connection device for fastening said modules comprises a cylindrical bush with a cavity for receiving said portion able to be engaged, of the corresponding module.

3. An apparatus according to claim 2, wherein said bush is oriented parallel to the sagittal plane.

4. An apparatus according to claim 1, wherein said connection device for fastening said modules comprises two cylindrical bushes with a cavity for receiving two portions able to be engaged, of the corresponding module.

5. An apparatus according to claim 4, wherein said bushes are disposed symmetrically to said plane (s—s).

6. An apparatus for dento-maxillo-facial orthodontics and orthopedics, the apparatus comprising:
    a base structure with connection portions for fixing the base structure to latero-posterior teeth of the superior arch transversely to the sagittal plane in correspondence of the palatal vault, said base structure having a plurality of arms extending orthogonally to the sagittal plane and with said connection portions including annular bands provided to allow a stable positioning of an arm for applying force on respective said latero-posterior teeth of the superior arch transversely to the sagittal plane in correspondence of the palatal vault for orthopedic therapy;
    a connection device connected to said base structure; and
    one or more orthodontic or orthopedic module, said one or more module having a portion able to be engaged with said connection device for fastening said one or more module relative to said base structure, wherein said one or more module is a mandibular condylar distractor fixed to said base structure.

7. An apparatus for dento-maxillo-facial orthodontics and orthopedics, the apparatus comprising:
    a base structure with connection portions for fixing the base structure to latero-posterior teeth of the superior arch transversely to the sagittal plane in correspondence of the palatal vault, said base structure having a plurality of arms extending orthogonally to the sagittal plane and with said connection portions including annular bands provided to allow a stable positioning of an arm for applying force on respective said latero-posterior teeth of the superior arch transversely to the sagittal plane in correspondence of the palatal vault for orthopedic therapy;
    a connection device connected to said base structure; and
    one or more orthodontic or orthopedic module, said one or more module having a portion able to be engaged with said connection device for fastening said one or more module relative to said base structure, wherein said one or more module is an extra-oral traction device fixed to said base structure.

8. An apparatus for dento-maxillo-facial orthodontics and orthopedics, the apparatus comprising:
    a base structure with connection portions for fixing the base structure to latero-posterior teeth of the superior arch transversely to the sagittal plane in correspondence of the palatal vault, said base structure having a plurality of arms extending orthogonally to the sagittal plane and with said connection portions including annular bands provided to allow a stable positioning of an arm for applying force on respective said latero-posterior teeth of the superior arch transversely to the sagittal plane in correspondence of the palatal vault for orthopedic therapy;
    a connection device connected to said base structure; and
    one or more orthodontic or orthopedic module, said one or more module having a portion able to be engaged with said connection device for fastening said one or more module relative to said base structure, wherein said one or more module is a lingual grid fixed to said base structure.

9. An apparatus for dento-maxillo-facial orthodontics and orthopedics, the apparatus comprising:
    a base structure with connection portions for fixing the base structure to latero-posterior teeth of the superior arch transversely to the sagittal plane in correspondence of the palatal vault, said base structure having a plurality of arms extending orthogonally to the sagittal plane and with said connection portions including annular bands provided to allow a stable positioning of an arm for applying force on respective said latero-posterior teeth of the superior arch transversely to the sagittal plane in correspondence of the palatal vault for orthopedic therapy;
    a connection device connected to said base structure; and
    one or more orthodontic or orthopedic module, said one or more module having a portion able to be engaged with said connection device for fastening said one or more module relative to said base structure, wherein said one or more module is a support for a device recording the mandibula's path fixed to said base structure.

10. An apparatus for dento-maxillo-facial orthodontics and orthopedics, the apparatus comprising:

a base structure with connection portions for fixing the base structure to latero-posterior teeth of the superior arch transversely to the sagittal plane in correspondence of the palatal vault, said base structure having a plurality of arms extending orthogonally to the sagittal plane and with said connection portions including annular bands provided to allow a stable positioning of an arm for applying force on respective said latero-posterior teeth of the superior arch transversely to the sagittal plane in correspondence of the palatal vault for orthopedic therapy;

a connection device connected to said base structure; and one or more orthodontic or orthopedic module, said one or more module having a portion able to be engaged with said connection device for fastening said one or more module relative to said base structure, wherein said one or more module is a roller for lingual reeducation fixed to said base structure.

11. An apparatus for dento-maxillo-facial orthodontics and orthopedics, the apparatus comprising:

a base structure with connection portions for fixing the base structure to latero-posterior teeth of the superior arch transversely to the sagittal plane in correspondence of the palatal vault, said base structure having a plurality of arms extending orthogonally to the sagittal plane and with said connection portions including annular bands provided to allow a stable positioning of an arm for applying force on respective said latero-posterior teeth of the superior arch transversely to the sagittal plane in correspondence of the palatal vault for orthopedic therapy;

a connection device connected to said base structure; and one or more orthodontic or orthopedic module, said one or more module having a portion able to be engaged with said connection device for fastening said one or more module relative to said base structure, wherein said one or more module is an interocclusal spacer fixed to said structure.

12. An apparatus for dento-maxillo-facial orthodontics and orthopedics, the apparatus comprising:

a base structure with connection portions for fixing the base structure to latero-posterior teeth of the superior arch transversely to the sagittal plane in correspondence of the palatal vault, said base structure having a plurality of arms extending orthogonally to the sagittal plane and with said connection portions including annular bands provided to allow a stable positioning of an arm for applying force on respective said latero-posterior teeth of the superior arch transversely to the sagittal plane in correspondence of the palatal vault for orthopedic therapy;

a connection device connected to said base structure; and one or more orthodontic or orthopedic module, said one or more module having a portion able to be engaged with said connection device for fastening said one or more module relative to said base structure, wherein said one or more module is a mandibular conditioner fixed to said structure.

13. An apparatus for dento-maxillo-facial orthodontics and orthopedics, the apparatus comprising:

a base structure with connection portions for fixing the base structure to latero-posterior teeth of the superior arch transversely to the sagittal plane in correspondence of the palatal vault, said base structure having a plurality of arms extending orthogonally to the sagittal plane and with said connection portions including annular bands provided to allow a stable positioning of an arm for applying force on respective said latero-posterior teeth of the superior arch transversely to the sagittal plane in correspondence of the palatal vault for orthopedic therapy;

one or more orthodontic or orthopedic module, said one or more module having an engageable portion; and fastening means for removable or irremovable fastening of said one or more orthodontic or orthopedic modules, said engageable portion being provided for engagement with said fastening means to fix said module relative to said base, said one or more module cooperating with the base structure when fastened to provide two orthopedic functional elements or to provide one orthopedic functional element and one orthodontic functional element, wherein said base structure includes an expansion screw with two movable blocks guided by two straight rods and associated with a screw drive which axially engages the two blocks and a plurality of modules are provided, each selectively connectable to said base structure via said fastening means, said modules being one or more of a mandibular condylar distractor fixed to said base structure, a lingual grid fixed to said base structure, a support for a device recording the mandibula's path fixed to said structure, an interocclusal spacer fixed to said structure, and a mandibular conditioner fixed to said structure.

14. An apparatus according to claim 13, wherein said fastening means comprises a cylindrical bush with a cavity for receiving said engageable portion, of the corresponding module.

15. An apparatus according to claim 14, wherein said bush is oriented parallel to the sagittal plane.

16. An apparatus according to claim 14, wherein said fastening means comprises two cylindrical bushes each with a cavity for receiving a respective one of two portions able to be engaged, of the corresponding module.

17. An apparatus according to claim 16, wherein said bushes are disposed symmetrically to said plane (s—s).

* * * * *